United States Patent [19]

Mixan et al.

[11] 4,101,546

[45] Jul. 18, 1978

[54] CYANATOTHIOMETHYLTHIO PYRAZINES

[75] Inventors: Craig E. Mixan; Christian T. Goralski, both of Midland, Mich.

[73] Assignee: The Dow Chemical Company, Midland, Mich.

[21] Appl. No.: 835,473

[22] Filed: Sep. 21, 1977

Related U.S. Application Data

[63] Continuation-in-part of Ser. No. 759,944, Jan. 17, 1977, abandoned, which is a continuation-in-part of Ser. No. 588,757, Jun. 29, 1975, abandoned.

[51] Int. Cl.$^2$ ............................................. C07D 241/04
[52] U.S. Cl. ........................................ 544/408; 71/92; 424/250; 544/409
[58] Field of Search ................................. 260/250 BN

[56] References Cited

U.S. PATENT DOCUMENTS 3,772,313  11/1973  Gizycki et al. .................. 260/296 C
3,919,228  11/1975  Gizycki et al. ............... 260/256.4 N

*Primary Examiner*—Jose Tovar
*Attorney, Agent, or Firm*—S. Preston Jones; C. Kenneth Bjork

[57] ABSTRACT

Compounds are prepared which correspond to the formula

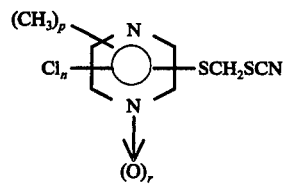

wherein $n$ represents an integer of 0 to 3; $p$ represents an integer of 0 to 2 and the sum of $n + p$ is an integer of 0 to 3; and $r$ is 0 or 1. These compounds have been found to be active as pesticides and find particular usage as fungicides, bactericides, nematocides and herbicides.

14 Claims, No Drawings

CYANATOTHIOMETHYLTHIO PYRAZINES

CROSS REFERENCE TO RELATED APPLICATIONS

This application is a continuation-in-part of Application Ser. No. 759,944 filed Jan. 17, 1977, now abandoned, which in turn is a continuation-in-part of Application Ser. No. 588,757 filed June 29, 1975, now abandoned.

SUMMARY OF THE INVENTION

The present invention is directed to compounds corresponding to the formula

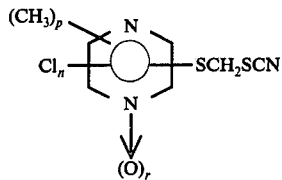

wherein $n$ represents an integer of 0 to 3; $p$ represents an integer of 0 to 2 and the sum of $n + p$ is an integer of 0 to 3; and $r$ is 0 or 1.

The pyrazinylthiocyanatomethylthio compounds of the present invention are crystalline solids or liquids. They are useful as pesticides for the control of various fungal, bacterial, nematode and plant pests such as, for example, Nutsedge, pigweeds, crabgrass, Johnson grass, barnyard grass, yellow foxtail, cocklebur, root-knot nematodes, *Staphylococcus aureus, Candida albicans, Trichophyton mentagrophytes, Pullularia pullulans, Rhizopus nigricans, mycobacterium phlei*, apple scab, bean mildew, and many other such pests.

The pyrazinylthiocyanatomethylthio compounds of the present invention can be prepared by a variety of methods. In one such method, the pyrazinylthiocyanatomethylthio compounds and their N-oxides can be prepared by reacting an appropriate chloro-substituted pyrazine or halo-substituted pyrazine N-oxide with an equimolar amount of sodium sulfide nonahydrate in a reaction medium or solvent followed by the reaction therewith with one mole of chloromethylthiocyanate. This reaction can be characterized as follows:

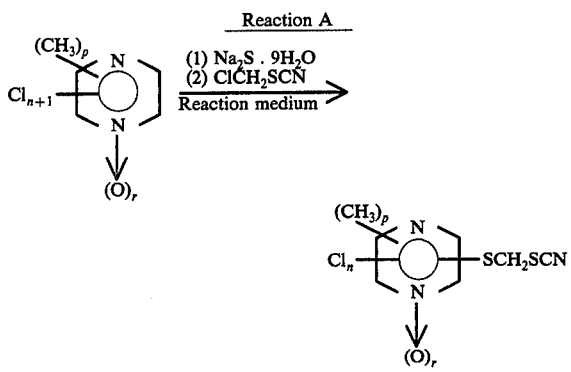

Wherein $n$, $p$ and $r$ are as hereinbefore defined.

In carrying out this reaction, the appropriate chloro-substituted pyrazine or its N-oxide is mixed with an equimolar amount of sodium sulfide nonahydrate in a reaction medium such as dimethylformamide, acetone, acetonitrile or dimethylsufloxide. The mixture is agitated for from about 4 to about 24 hours at a temperature in the range of from about 25° to about 70° C. After this period of time, an equimolar amount of a chloromethylthiocyanate is added to the mixture and the reaction mixture agitated at a temperature in the range of from 25°-70° C for an additional 1 to 4 hours. The solvent is removed by evaporation under reduced pressure and the residue thereafter dissolved in a water/solvent mixture. Representative solvents include chloroform and other conventional halogenated hydrocarbons. The mixture separates into organic and aqueous phases. The aqueous portion is acidified with a dilute mineral acid and extracted with one of the above solvents and the organic extracts combined. The combined extracts are washed with a saturated sodium bicarbonate solution followed by washing with a saturated sodium chloride solution and dried. The solvent is removed by evaporation leaving the crude product as a residue. The product is thereafer purified, if desired, by conventional practices of solvent recrystallization from one of the hereinabove set forth solvents or by conventional column chromatography.

In an alternative procedure, the substituted pyrazine compounds can be prepared by the reaction of an appropriate chloromethylthiopyrazine with an equimolar amount of an alkali thiocyanate in a solvent such as dimethylformamide, acetone, acetonitrile or dimethylsulfoxide. This reaction can be characterized as follows:

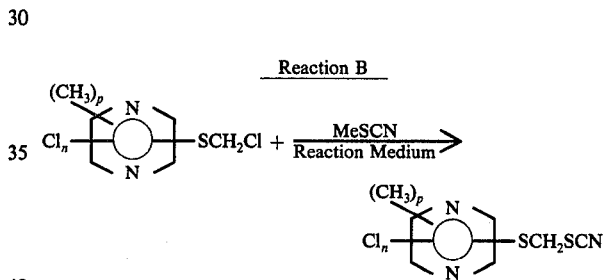

wherein $p$ and $n$ are as hereinbefore defined and Me represents sodium, potassium, lithium or cesium.

In carrying out this reaction, the appropriate substituted chloromethylthiopyrazine is mixed with an equimolar amount and preferably a 10 to 50 percent excess of the alkali metal thiocyanate in one of the reaction mediums set forth hereinabove. The mixture is agitated at a temperature of from about 50° to about 100° C until the reaction is complete, usually in from about 1 to 7 days. The solvent (reaction medium) is removed by evaporation under reduced pressure and the residue dissolved in a water/solvent mixture. Representative solvents include chloroform and other conventional halogenated hydrocarbons. The mixture separates into organic and aqueous phases. The aqueous portion is solvent extracted and the organic extracts combined. The extracts are washed with a saturated sodium bicarbonate solution followed by washing with a saturated sodium chloride solution and dried. The solvent is removed by evaporation and the crude product which is left as a residue is purified, if desired, by solvent recrystallization or conventional column chromatography.

The chloromethylthiopyrazines employed as starting materials can be prepared by the reaction of an appropriate methylthio substituted pyrazine with an excess of phosphorus pentachloride under reflux conditions for about 1 week. At the completion of the reaction, the reaction mixture is poured into ice water and extracted with a solvent such as chloroform. The extract is washed with a saturated sodium bicarbonate solution followed by washing with a saturated sodium chloride solution and dried. The solvent is removed by evaporation under reduced pressure leaving the product as a residue which can be purified, if desired, by recrystallization from solvents such as hexane and other conventional hydrocarbon solvents.

The substituted methylthiopyrazines are well known and can be prepared by procedures known in the art such as the method taught in U.S. Pat. No. 3,452,016 whereby a halogen substituted pyrazine is reacted with an equimolar proportion of an alkali metal mercaptide. The reaction proceeds readily at temperatures of from about 10° to about 80° C with the formation of an alkali metal halide as a byproduct. The reaction is conveniently carried out in a lower alkanol solvent. The products can be isolated from the reaction mixture by conventional procedures such as precipitation in water and solvent extraction and may be further purified by recrystallization.

While the present invention is mainly directed to the preparation of the final products using separate reaction steps and procedures, it is within the scope of this invention to prepare the claimed compounds in sequential steps from various intermediates in the same reaction vessel.

DESCRIPTION OF PREFERRED EMBODIMENTS

The following examples illustrate the invention, but as such, are not to be construed as limiting the same.

EXAMPLE I 3,5,6-Trichloro-2-methylthiopyrazine

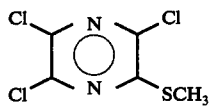

A solution was prepared by dissolving 25 grams (0.115 mole) of tetrachloropyrazine in 300 milliliters of methanol. To this solution was added over a 90 minute period, a solution of 115 milliliters of ~1.0 molar sodium mercaptide in methanol. The temperature was maintained below 20° C during the addition. The reaction mixture was stirred at room temperature overnight and thereafter poured into 400 milliliters of water. The precipitate which formed was removed by filtration and recrystallized from hexane. The 3,5,6-trichloro-2-methylthiopyrazine product was recovered in a yield of 7.11 grams, 27 percent of theoretical, and melted at 45°–47° C.

EXAMPLE II 3,5,6-Trichloro-2-(chloromethylthio)pyrazine

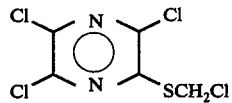

A mixture of 22.6 grams (0.1 mole of 3,5,6-trichloro-2-methylthiopyrazine and 20 grams (0.1 mole) of phosphorus pentachloride were heated at reflux (170° C) in an oil bath until the phosphorus pentachloride ceased to sublime. An additional 18 grams (0.095 mole) of phosphorus pentachloride were incrementally added until the reaction was complete (6 days). The reaction mixture was poured into ice water and extracted with chloroform. The extract was washed with a saturated sodium bicarbonate solution followed by washing with a saturated sodium chloride solution and dried over anhydrous magnesium sulfate. The chloroform was removed by evaporation and the yellow-orange oil which remained was recrystallized from hexane. The 3,5,6-trichloro-2-(chloromethylthio)pyrazine product was recovered in a yield of 8.0 grams (~30 percent of theoretical) and melted at 68°–70° C. Upon analysis, the product was found to have carbon, hydrogen and nitrogen contents of 22.80, 0.88 and 10.83 percent, respectively, as compared with the theoretical contents of 22.72, 0.76 and 10.61 percent, respectively, calculated for the above-named compound.

EXAMPLE III 3,5,6-Trichloro-2-(thiocyanatomethylthio)pyrazine

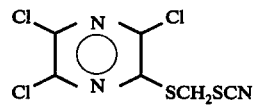

To a solution of 4.0 grams (0.015 mole) of 3,5,6-trichloro-2-(chloromethylthio)pyrazine in 75 milliliters of dimethylformamide was added 1.6 grams (0.02 mole) of sodium thiocyanate. The reaction mixture was heated to 75° C and monitored by nuclear magnetic resonance spectroscopy. An additional 4.8 grams (0.06 mole) of sodium thiocyanate was incrementally added until the reaction was complete (5 days). The solvent was removed by evaporation under reduced pressure and the residue remaining was dissolved in a mixture of water and chloroform. Two phases formed and the aqueous phase was extracted with chloroform. The organic fractions were combined and washed with a saturated sodium bicarbonate solution followed by washing with a saturated sodium chloride solution and dried over anhydrous magnesium sulfate. The solvent was removed by evaporation and the crude 3,5,6-trichloro-2-(thiocyanatomethylthio)pyrazine product was purified by elution with chloroform from a silica gel column. The product was recovered in a yield of 0.32 grams (7.5 percent of theoretical) and melted at 90°–93° C. Upon analysis, the product was found to have carbon, hydrogen, nitrogen and sulfur contents of 25.60, 1.01, 14.29 and 22.60 percent, respectively, as compared with the theoretical contents of 25.13, 0.70, 14.66 and 22.34 percent, respectively, calculated for the above-named structure.

EXAMPLE IV

6-Chloro-2-(thiocyanatomethylthio)pyrazine

To a vigorously stirred solution of 9.6 grams (0.04 mole) of sodium sulfide nonahydrate in 100 milliliters of dimethylformamide was gradually added 6.0 grams (0.04 mole) of 2,6-dichloropyrazine in 50 milliliters of dimethylformamide. The mixture was stirred overnight at 55° C and thereafter 4.3 grams (0.04 mole) of chloromethylthiocyanate was added. After a 4-hour reaction period, the dimethylformamide was rmoved by evaporation under reduced pressure and the residue dissolved in a mixture of water and chloroform. A two-phase mixture formed and the aqueous phase was acidified with hydrochloric acid and extracted with chloroform. The organic phases were combined and washed with both a saturated sodium bicarbonate solution and a saturated sodium chloride solution. The solvent was removed by evaporation and the crude 6-chloro-2-(thiocyanatomethylthio)pyrazine was purified by elution with chloroform from a silica gel column. The product was recovered in a yield of 3.5 grams (40 percent of theoretical) and melted at 61°–66° C. Upon analysis, the product was found to have carbon, hydrogen, nitrogen and sulfur contents of 33.10, 1.90, 19.04 and 29.70 percent, respectively, as compared with the theoretical contents of 33.10, 1.84, 19.31 and 29.43 percent, respectively, calculated for the above-named compound.

By following the above-preparative procedures, and employing the appropriate starting materials, the following compounds are prepared.

2-(Thiocyanatomethylthio)pyrazine, a liquid having a boiling point of 140° C at 1.0 millimeter of mercury;

3-Methyl-2-(thiocyanatomethyltho)pyrazine, having a molecular weight of 196.27;

3,5-Dichloro-2-(thiocyanatomethylthio)pyrazine, having a molecular weight of 252.14;

3,6-Dimethyl-2-(thiocyanatomethylthio)pyrazine, having a melting point of 69°–71° C; and 3-Chloro-2-(thiocyanatomethylthio)pyrazine, a liquid having a boiling point of 130° C at 0.5 millimeters of mercury.

3,5-Dichloro-6-methyl-2-(thiocyanatomethylthio)pyrazine, having a molecular weight of 266.17.

EXAMPLE V 3-(Thiocyanatomethylthio)pyrazine-1-oxide

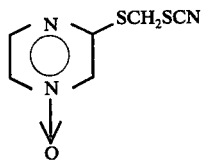

To a vigorously stirred solution of 9.6 grams (0.04 mole) of sodium sulfide nonahydrate in 100 milliliters of dimethylformamide was gradually added 5.2 grams (0.04 mole) of 3-chloropyrazine-1-oxide in 50 milliliters of dimethylformamide. The reaction mixture was stirred overnight at 45°–50° C. Thereafter, 4.3 grams (0.04 mole) of chloromethylthiocyanate were gradually added and the mixture stirred for 4 hours. At the completion of the reaction, the dimethylformamide was removed by evaporation under reduced pressure and the residue was dissolved in a mixture of water and chloroform. Two phases formed and the aqueous phase was acidified with hydrochloric acid and extracted with chloroform. The organic portions were combined and washed with both a saturated sodium bicarbonate solution and a saturated sodium chloride solution and dried over magnesium sulfate. The chloroform was thereafter removed by evaporation leaving the 3-(thiocyanatomethylthio)pyrazine-1-oxide as a residue. The product was recrystallized from methanol and was recovered in a yield of 4.75 grams (60 percent of theoretical). The product melted at 104°–106° C and upon analysis was found to have carbon, hydrogen, nitrogen and sulfur contents of 36.40, 2.66, 20.59 and 32.20 percent, respectively, as compared with the theoretical contents of 36.18, 2.51, 21.11 and 32.16 percent, respectively, as calculated for the above-named compound.

EXAMPLE VI 2,6-Dichloropyrazine-1-oxide

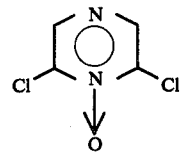

To a stirred solution of 15 grams (0.1 mole) of 2,6-dichloropyrazine in 120 milliliters of concentrated sulfuric acid, maintained at 5° C, was gradually added 30 grams (0.11 mole) of potassium persulfate. The reaction mixture was stirred overnight at room temperature and thereafter poured into 400 milliliters of ice water. The resulting solution was thoroughly extracted with chloroform and the extract washed with both a saturated sodium bicarbonate solution and a saturated sodium chloride solution and dried over magnesium sulfate. The chloroform was thereafter removed by evaporation leaving the 2,6-dichloropyrazine-1-oxide as a white solid residue. The product was recrystallized from methanol and was recovered in a yield of 10.2 grams (62 percent of theoretical). The product melted at 120°–123.5° C, and upon analysis was found to have carbon, hydrogen, nitrogen and chlorine contents of 29.20, 1.42, 17.01 and 42.40 percent, respectively, as compared with the theoretical contents of 29.09, 1.21, 16.97 and 43.03 percent, respectively, calculated for the above-named compound.

EXAMPLE VII

6-Chloro-2-(thiocyanatomethylthio)pyrazine-1-oxide

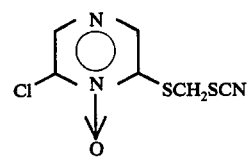

To a vigorously stirred solution of 9.6 grams (0.04 mole) of sodium sulfide nonahydrate in 100 milliliters of dimethylformamide was gradually added 6.6 grams (0.04 mole) of 2,6-dichloropyrazine-1-oxide in 50 milliliters of dimethylformamide. The reaction mixture was stirred overnight at ~40° C. Thereafter, 4.3 grams (0.04 mole) of chloromethylthiocyanate were gradually added and the mixture stirred for 4 hours. At the completion of the reaction, the dimethylformamide was removed by evaporation under reduced pressure and the residue was dissolved in a mixture of water and chloroform. Two phases formed and the aqueous phase was acidified with hydrochloric acid and extracted with chloroform. The organic portions were combined and washed with both a saturated sodium bicarbonate solution and a saturated sodium chloride solution and dried over magnesium sulfate. The chloroform was thereafter removed by evaporation leaving the 6-chloro-2-(thiocyanatomethylthio)pyrazine-1-oxide as a residue. The product was recrystallized from methanol and was recovered in a yield of 3.0 grams (32 percent of theoretical). The product melted at 95°–98° C and upon analysis was found to have carbon, hydrogen, chlorine, nitrogen and sulfur contents of 31.00, 1.82, 15.20, 18.04 and 27.20 percent, respectively, as compared with the theoretical contents of 30.84, 1.71, 15.20, 17.99 and 27.41 percent, respectively, as calculated for the above-named compound.

EXAMPLE VIII 2,3-Dichloropyrazine-1-oxide

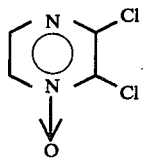

To a stirred solution of 15 grams (0.1 mole) of 2,3-dichloropyrazine in 120 milliliters of concentrated sulfuric acid, maintained at 5° C, was gradually added 30 grams (0.11 mole) of potassium persulfate. The reaction mixture was stirred overnight at room temperature and thereafter poured into 400 milliliters of ice water. The resulting solution was thoroughly extracted with chloroform and the extract washed with both a saturated sodium bicarbonate solution and a saturated sodium chloride solution and dried over magnesium sulfate. The chloroform was thereafter removed by evaporation leaving the 2,3-dichloropyrazine-1-oxide as a white solid residue. The product was recrystallized from methanol and was recovered in a yield of 14.0 grams (85 percent of theoretical). The product melted at 104°–106° C, and upon analysis was found to have carbon, hydrogen, nitrogen and chlorine contents of 29.40, 1.41, 17.08 and 43.20 percent, respectively, as compared with the theoretical contents of 29.09, 1.21, 16.97 and 43.03 percent, respectively, calculated for the above-named compound.

By following the above-preparative procedures and employing the appropriate starting materials, the following compounds are prepared.

3-Chloro-2-(thiocyanatomethylthio)pyrazine-1-oxide, melting at 112°–114° C;
2-(Thiocyanatomethylthio)pyrazine-1-oxide, melting at 114°–116° C;
2,5-Dimethyl-3-(thiocyanatomethylthio)pyrazine-1-oxide, melting at 118°–120° C;
3,5-Dichloro-2-(thiocyanatomethylthio)pyrazine-1-oxide, having a molecular weight of 268.14;
3,6-Dimethyl-2-(thiocyanatomethylthio)pyrazine-1-oxide, melting at 82°–83° C; and
3,5-Dichloro-6-methyl-2-(thiocyanatomethylthio)-pyrazine-1-oxide, having a molecular weight of 282.17.

The pyrazine compounds of the present invention are useful as pesticides and have particular utility as fungicides, bactericides, and herbicidal agents for the control of various undesirable weed pests. In such applications, the pest to be controlled is contacted with a pesticidal amount of one or more of the compounds of the invention. For the control of bacteria and fungi, the organism is contacted with a pesticidal amount, which is also an antimicrobial amount of the compound. For control of weed pests, a pesticidal amount, which is also a herbicidal amount, is employed.

For all such uses, the present pyrazine compounds can be employed in an unmodified form or they can be dispersed on a finely-divided solid and employed as dusts or dispersed in water with or without the aid of a surface-active agent and the resulting aqueous suspensions employed as drenches or sprays. In other procedures, the products are employed as active constituents in solvent solutions, in oil-in-water or water-in-oil emulsions, or in aqueous dispersions. All such ingredients and adjuvants cooperate with the active component so as to facilitate the invention and obtain an improved and outstanding result.

The foregoing augmented compositions are adapted to be formulated as liquid or solid concentrates and subsequently diluted with additional liquid or solid adjuvants to produce the ultimate treating composition. Suitable emulsifiable liquid concentrates are formulations of the active pyrazine compound in a suitable organic solvent, therefor, such as alcohols, alkyl ethers of glycols and polyglycols, ketones, aromatics and petroleum distillates, together with an ionic or non-ionic emulsifying agent for a mixture thereof. Such emulsions are preferably designed such that they are self-dispersing with good stability characteristics. The dusts and dust concentrates can be prepared by dispersing the active toxicant compounds in and on a finely-divided inert solid support such as diatomaceous earth, bentonite, fuller's earth, attapulgite and similar clays. For the preparation of wettable powders, the solid carrier may be mechanically ground in admixture with the active component hereof and a surface-active dispersing agent.

The compound of the invention or compositions containing them as toxic constituents can be included in and on plaster, ink, wallboard, wood, textiles, paper, adhesives, soaps, synthetic detergents, cutting oils, polymeric materials, embalming fluids, oil paints and latex paints to prevent the attack of various fungal pests and the subsequent economic loss due to the degradation of such product by microorganisms. Also the compounds can be distributed in textiles or cellulosic materials to preserve and protect such products from the attack of the organisms of rot, mold and decay.

Any of the foregoing compositions can be distributed so as to contact pests with a pesticidal amount of one or more of the active compounds. This amount depends largely upon the manner of distribution, the type of pest being treated and its extent or severity of development and the degree of control desired or required for any particular purpose. Generally, the effective or pesticidal dosage ranges from 1 to 10,000 or more parts of toxicant per million parts of applied composition. For the control of various weed and other plant pests by the method of topical application, the effective herbicidal dosage ranges from about 10 to 5000 parts of the pyrazine compound per million parts of the composition applied to the plant. For the control of higher plants in soil, the active pyrazine compounds hereof ordinarily are distributed in soil in amounts of from about 0.1 to 50 lbs or more per acre so as to contact seeds and emerging seedlings of the vegetation to be controlled. For the control of bacteria and fungi, the active compounds usually are applied to the growth media of said organisms in amounts to provide from about 10 or less to about 5000 or more parts by weight of the active substituted pyrazine compound per million parts of the ultimate treating composition.

The exact concentration of the toxicant to be employed in the treating compositions is not critical and may vary considerably provided the required dosage of the effective agent is supplied in the ink, adhesive, soap, cutting oil, polymeric material, paint, textile, paper, or growth medium. The concentration of toxicant in liquid compositions generally is from about 0.0001 to 50 percent by weight. Concentrations up to 95 percent by weight are oftentimes conveniently employed, particularly in concentrate compositions. In dusts, the concentrations of the toxicant can be from about 0.1 to 95 percent by weight. In compositions to be employed as concentrates, the toxicants can be present in a concentration of from 5 to 98 percent by weight. For use as a spray, it is often convenient to apply the compounds as wettable powders.

In a representative operation, each of the compounds 3-(thiocyanatomethylthio)pyrazine-1-oxide, 2-(thiocyanatomethylthio)pyrazine, 3-chloro-2-(thiocyanatomethylthio)pyrazine, 2-(thiocyanatomethylthio)pyrazine-1-oxide, 3-chloro-2-(thiocyanatomethylthio)pyrazine-1-oxide, 3,6-dimethyl-2-(thiocyanatomethylthio)pyrazine, 3,6-dimethyl-2-(thiocyanatomethylthio)pyrazine-1-oxide, 2,5-dimethyl-3-(thiocyanatomethylthio)pyrazine-1-oxide and 3,5,6-trichloro-2-(thiocyanatomethylthio)pyrazine were found to give 100 percent kill and control of the organisms *Candida albicans, Trichophyton mentagrophytes, Mycobacterium phlei, Rhizopus nigricans, Ceratocystis IPS, Trichoderm Sp. Madison P-42, Candida Pelliculosa,* and *Pullularia pullulans* when employed, as the sole toxicant, in a nutrient agar at a concentration of 100 parts by weight of the compound per million parts of agar.

In another operation, 6-chloro-2-(thiocyanatomethylthio)pyrazine-1-oxide was found to give 100 percent kill and control of the organisms *Pseudomunas Sp. Strain 10, Staphylococcus aureus, Trichophyton mentagrophytes, Penicill chrysogesum, Aspergillus niger* and *Bacillus subtilis* when employed, as the sole toxicant, in a nutrient agar at a concentration of 100 parts by weight of the compound per million parts of agar.

In another such operation, each of the compounds 3-(thiocyanatomethylthio)pyrazine-1-oxide, 2-(thiocyanatomethylthio)pyrazine-1-oxide, 3-chloro-2-(thiocyanatomethylthio)pyrazine-1-oxide, and 3,6-dimethyl-2-(thiocyanatomethylthio)pyrazine-1-oxide were found to give 100 percent kill and control of the organisms *Escherichia coli, Bacillus subtilis, Aerobacter erogenes,* and *Salmonella typhosa* when employed, as the sole toxicant, in a nutrient agar at a concentration of 100 parts by weight of the compound per million parts of agar.

In other operations, each of the compounds 3-(thiocyanatomethylthio)pyrazine-1-oxide, 2-(thiocyanatomethylthio)pyrazine, 3-chloro-2-(thiocyanatomethylthio)pyrazine, and 2-(thiocyanatomethylthio)pyrazine-1-oxide when applied, as the sole toxicant, in an aqueous composition at a concentration of 4000 parts by weight per million parts of the ultimate composition, were found to give at least 99 percent kill and control of the causative organism of bean mildew.

In another operation, 3-chloro-2-(thiocyanatomethylthio)pyrazine-1-oxide, when employed as the sole toxicant constituent in an aqueous dispersion at a concentration of 12 parts per million by weight of the ultimate dispersion, when applied to soil infested with root-knot nematodes, gave 100 percent kill and control of said nematodes.

In other operations, 3-(thiocyanatomethylthio)pyrazine-1-oxide as the sole toxicant in an aqueous composition at a concentration of 100 parts by weight of the ultimate composition give substantially complete kill and control of the causative organisms of downy mildew and rice blast.

In another operation, each of the compounds 2-(thiocyanatomethylthio)pyrazine, 3-chloro-2-(thiocyanatomethylthio)pyrazine, 2-(thiocyanatomethylthio)pyrazine and 3,6-dimethyl-2-(thiocyanatomethylthio)pyrazine-1-oxide when employed, as the sole toxicant, in an aqueous composition at a concentration of 4000 parts per million by weight of the ultimate composition gave 100 percent kill and control of pigweeds.

In another such operation, each of the compounds 2-(thiocyanatomethylthio)pyrazine and 2-(thiocyanatomethylthio)pyrazine-1-oxide when employed, as the sole toxicant, in an aqueous composition at a concentration of 4000 parts per million by weight of the ultimate composition gave substantially complete kill and control of barnyard grass, bindweed, yellow foxtail and velvet leaf.

What is claimed is:

1. A compound corresponding to the formula

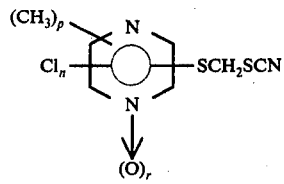

wherein n represents an integer of 0 to 3, p represents an integer of 0 to 2 and the sum of $n + p$ is an integer of 0 to 3; and r is 0 or 1.

2. A compound as defined in claim 1 wherein r is 0.

3. A compound as defined in claim 1 wherein r is 1.

4. The compound as defined in claim 2 which is 2-(thiocyanatomethylthio)pyrazine.

5. The compound as defined in claim 2 which is 3-chloro-2-(thiocyanatomethylthio)pyrazine.

6. The compound as defined in claim 2 which is 6-chloro-2-(thiocyanatomethylthio)pyrazine.

7. The compound as defined in claim 2 which is 3,5,6-trichloro-2-(thiocyanatomethylthio)pyrazine.

8. The compound as defined in claim 2 which is 3,6-dimethyl-2-(thiocyanatomethylthio)pyrazine.

9. The compound as defined in claim 3 which is 3-(thiocyanatomethylthio)pyrazine-1-oxide.

10. The compound as defined in claim 3 which is 2-(thiocyanatomethylthio)pyrazine-1-oxide.

11. The compound as defined in claim 3 which is 6-chloro-2-(thiocyanatomethylthio)pyrazine-1-oxide.

12. The compound as defined in claim 3 which is 3-chloro-2-(thiocyanatomethylthio)pyrazine-1-oxide.

13. The compound as defined in claim 3 which is 2,5-dimethyl-3-(thiocyanatomethylthio)pyrazine-1-oxide.

14. The compound as defined in claim 3 which is 3,6-dimethyl-2-(thiocyanatomethylthio)pyrazine-1-oxide.

* * * * *

UNITED STATES PATENT AND TRADEMARK OFFICE
CERTIFICATE OF CORRECTION

PATENT NO. : 4,101,546
DATED : July 18, 1978
INVENTOR(S) : Craig E. Mixan, et al.

It is certified that error appears in the above-identified patent and that said Letters Patent are hereby corrected as shown below:

Column 2, line 20, "thereafer" should read -- thereafter --;

Column 5, line 4 "rmoved" should read -- removed --;

Column 5, line 28, "(thiocyanatomethyltho)" should read --(thiocyanatomethylthio)--;

Column 8, line 25, "for" should read -- or --;

Column 9, line 50, "ero-" should read -- aero- --.

Signed and Sealed this

Twenty-seventh Day of March 1979

[SEAL]

Attest:

RUTH C. MASON
Attesting Officer

DONALD W. BANNER
Commissioner of Patents and Trademarks